US010229353B2

(12) United States Patent
Geissinger et al.

(10) Patent No.: US 10,229,353 B2
(45) Date of Patent: Mar. 12, 2019

(54) RFID TAG ON STRETCHABLE SUBSTRATE

(71) Applicant: 3M INNOVATIVE PROPERTIES COMPANY, St. Paul, MN (US)

(72) Inventors: John D. Geissinger, Austin, TX (US); Robin E. Gorrell, Round Rock, TX (US); Howard M. Kaplan, Oak Park, CA (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 15/328,675

(22) PCT Filed: Jul. 10, 2015

(86) PCT No.: PCT/US2015/039925
§ 371 (c)(1),
(2) Date: Jan. 24, 2017

(87) PCT Pub. No.: WO2016/018585
PCT Pub. Date: Feb. 4, 2016

(65) Prior Publication Data
US 2017/0213123 A1 Jul. 27, 2017

Related U.S. Application Data

(60) Provisional application No. 62/031,581, filed on Jul. 31, 2014.

(51) Int. Cl.
*G06K 7/08* (2006.01)
*G06K 19/06* (2006.01)
(Continued)

(52) U.S. Cl.
CPC ........ *G06K 19/07773* (2013.01); *A61B 5/117* (2013.01); *G06K 19/07* (2013.01);
(Continued)

(58) Field of Classification Search
USPC .......................... 235/451, 488, 492
See application file for complete search history.

(56) References Cited

U.S. PATENT DOCUMENTS

| 4,369,557 A | 1/1983 | Vandebult |
| 5,088,483 A | 2/1992 | Heinecke |

(Continued)

FOREIGN PATENT DOCUMENTS

| EP | 0821406 | 1/1998 |
| EP | 2214183 | 8/2010 |

(Continued)

OTHER PUBLICATIONS

Kim, "Epidermal Electronics," Science, Aug. 2011, vol. 333, No. 6044, pp. 838-843.

(Continued)

*Primary Examiner* — Tuyen K Vo
(74) *Attorney, Agent, or Firm* — Clifton F. Richardson

(57) ABSTRACT

A radio frequency identification tag including a stretchable substrate (105) and an antenna (110) having a plurality of substantially concentric loops (140) disposed on the substrate is described. A radius of curvature of the antenna along at least 90% of each loop of the antenna may be greater than about 0.1 mm and less than about 5 mm. The antenna includes a first terminal (124) disposed within an innermost loop (145) of the antenna and a second terminal (126) disposed outside an outermost loop (147) of the antenna (110). The first terminal (124) is in electrical communication with a first end (120) of the antenna and the second terminal (126) is in electrical communication with a second end (122) of the antenna. The radio frequency identification tag may include an electrode making electrical connections with the first and second terminals.

20 Claims, 10 Drawing Sheets

(51) Int. Cl.
  *G06K 19/077*  (2006.01)
  *G06K 19/07*   (2006.01)
  *H01Q 1/22*    (2006.01)
  *H01Q 1/36*    (2006.01)
  *H01Q 7/00*    (2006.01)
  *A61B 5/117*   (2016.01)

(52) U.S. Cl.
  CPC ....... *G06K 19/077* (2013.01); *G06K 19/0723* (2013.01); *H01Q 1/2225* (2013.01); *H01Q 1/36* (2013.01); *H01Q 7/00* (2013.01); *A61B 2562/08* (2013.01)

(56) References Cited

U.S. PATENT DOCUMENTS

| | | | |
|---|---|---|---|
| 5,738,642 | A | 4/1998 | Heinecke |
| 6,407,669 | B1 | 6/2002 | Brown |
| 6,693,541 | B2 | 2/2004 | Egbert |
| 7,969,307 | B2 | 6/2011 | Peeters |
| 2004/0103808 | A1 | 6/2004 | Lochun |
| 2005/0133131 | A1 | 6/2005 | Starinshak |
| 2006/0043199 | A1 | 3/2006 | Baba |
| 2006/0071084 | A1* | 4/2006 | Detig ............... G06K 19/07749 235/492 |
| 2006/0290513 | A1* | 12/2006 | Shanton ........... G06K 19/07749 340/572.7 |
| 2007/0035466 | A1* | 2/2007 | Coleman .......... G06K 19/07718 343/895 |
| 2008/0224940 | A1 | 9/2008 | Sugiyama |
| 2008/0301936 | A1* | 12/2008 | Van De Ven ........ G06K 19/077 29/852 |
| 2009/0032602 | A1 | 2/2009 | Nishi |
| 2009/0079568 | A1* | 3/2009 | Forster ............ G06K 19/07749 340/572.1 |
| 2011/0114734 | A1 | 5/2011 | Tiedmann |
| 2013/0041235 | A1 | 2/2013 | Rogers |
| 2013/0245388 | A1 | 9/2013 | Rafferty |
| 2013/0297301 | A1 | 11/2013 | Albert |
| 2014/0002325 | A1 | 1/2014 | Matsushita |
| 2014/0097944 | A1* | 4/2014 | Fastert ................. G06K 19/027 340/10.51 |
| 2015/0286913 | A1* | 10/2015 | Fastert ................. G06K 19/027 374/163 |

FOREIGN PATENT DOCUMENTS

| | | |
|---|---|---|
| JP | 08-129630 | 5/1996 |
| WO | WO 2014-015917 | 1/2014 |
| WO | WO 2016-018777 | 2/2016 |

OTHER PUBLICATIONS

Son, "Multifunctional Wearable Devices for Diagnosis and Therapy of Movement Disorders," Nature Nanotechnology, May 2014, vol. 9, pp. 397-404.

Warmann, "Google: Motorola's Tattoos could Replace Passwords," [retrieved from the internet on Aug. 1, 2014], URL < http://www.telegraph.co.uk/technology/mobile-phones/10090863/Google-Motorolas-tattoos-could-replace-passwords.html> 4 pages.

International Search Report for PCT International Application No. PCT/US2015/039925, dated Oct. 27, 2015, 5 pages.

International Search Report for PCT International Application No. PCT/US2015/042171, dated Mar. 21, 2016, 7 pages.

* cited by examiner

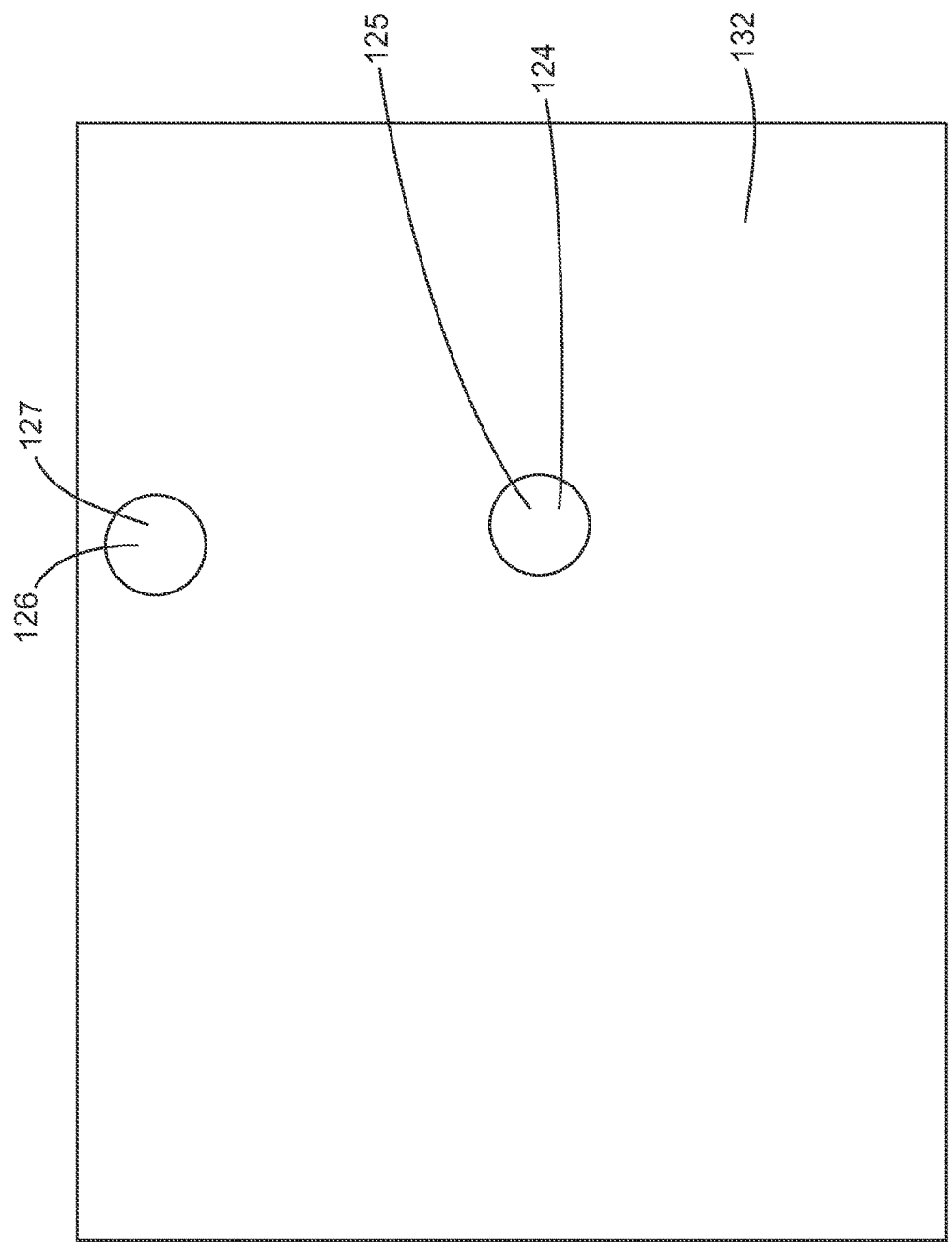

RFID TAG ON STRETCHABLE SUBSTRATE

BACKGROUND

Radio frequency identification (RFID) tags can be used for authentication. It may be desired to attach electronics that can be used for authentication to human skin. However, conventional RFID antennas may not provide sufficient flexibility for use in an RFID tag attached to human skin or may be prone to breaking when subject to the flexing or stretching associated with skin movement.

SUMMARY

In some aspects of the present description, a radio frequency identification tag is provided that includes a stretchable substrate having opposite major top and bottom surfaces, an antenna having a plurality of substantially concentric loops disposed on the major top surface, a first terminal, a second terminal, a dielectric layer printed on the antenna leaving at least portions of the first and second terminals exposed, and an electrically conductive ink printed on and between the exposed portions of the first and second terminals and electrically connecting the first and second terminals. The antenna includes an innermost loop and an outermost loop and a radius of curvature of the antenna along at least 90% of each loop of the antenna is greater than about 0.1 mm and less than about 5 mm. The first terminal is disposed within the innermost loop and is in electrical communication with a first end of the antenna. The second terminal is disposed outside the outermost loop and is in electrical communication with a second end of the antenna. The dielectric layer prevents the conductive ink from contacting any of the loops of the antenna.

In some aspects of the present description, a radio frequency identification tag is provided that includes a stretchable substrate having opposite major top and bottom surfaces, an antenna having a spiral form disposed on the major top surface and having a radius of curvature along at least 95% of an entire length of the antenna between first and second ends of the antenna greater than about 0.1 mm and less than about 4 mm, a first terminal disposed on the top surface and in electrical communication with the first end, a second terminal disposed on the top surface and in electrical communication with the second end, a first attachment area on the major bottom surface corresponding to and aligned with the first terminal, a second attachment area on the major bottom surface corresponding to and aligned with the second terminal, and a conductive wire having first and second ends attached to the respective first and second attachment areas and making crimp connections with the respective first and second terminals.

In some aspects of the present description, a radio frequency identification tag is provided that includes a first stretchable substrate having opposite major top and bottom surfaces, an antenna having a spiral form disposed on the major top surface and having a length between first and second ends, a first terminal disposed on the major top surface and in electrical communication with the first end, a second terminal disposed on the major top surface and in electrical communication with the second end, a second substrate having opposite major top and bottom surfaces, and a meandering electrode disposed on one of the major top and bottom surfaces of the second substrate. The second substrate is discrete from the first stretchable substrate and one of the major top and bottom surfaces of the second substrate faces one of the major top and bottom surfaces of the first stretchable substrate. The meandering electrode has first and second electrode ends in registration and making electrical connections with the respective first and second terminals.

In some aspects of the present description, a radio frequency identification tag is provided that includes a stretchable substrate having opposite major top and bottom surfaces, an antenna having a plurality of substantially concentric loops disposed on the major top surface and including an innermost loop and an outermost loop, a first terminal disposed within the innermost loop and in electrical communication with a first end of the antenna, a second terminal disposed outside the outermost loop and in electrical communication with a second end of the antenna, a dielectric layer printed on the antenna leaving at least portions of the first and second terminals exposed, and an electrically conductive wire. A first end of the wire is attached to and makes electrical connection with the first terminal, and a second end of the wire is attached to and makes electrical connection with the second terminal. A radius of curvature of the antenna along at least 95% of each loop of the antenna is greater than about 0.1 mm and less than about 4 mm. A gap is formed between the dielectric layer and the wire and the dielectric layer prevents the wire from contacting any of the loops of the antenna.

In some aspects of the present description, a radio frequency identification tag is provided that includes a stretchable substrate folded along a fold line to form top and bottom stretchable fold portions. Each fold portion has major top and bottom surfaces, and the major top surface of the bottom fold portion faces the major bottom surface of the top fold portion. The radio frequency identification tag also includes an antenna having a spiral form disposed on the major top surface of the top fold portion and having a length between first and second ends, a first terminal disposed on the major top surface of the top fold portion and in electrical communication with the first end of the antenna, a second terminal disposed on the major top surface of the top fold portion and in electrical communication with the second end of the antenna, and a meandering electrode disposed on the major bottom surface of the bottom fold portion. The meandering electrode has first and second electrode ends making crimp connections with the respective first and second terminals.

In some aspects of the present description, a radio frequency identification tag is provided that includes a stretchable substrate folded along a fold line to form top and bottom stretchable fold portions facing each other, an antenna having a length between first and second ends of the antenna disposed on a major first surface of the top fold portion, a first terminal disposed on the major first surface of the top fold portion and in electrical communication with the first end of the antenna, a second terminal disposed on the major first surface of the top fold portion and in electrical communication with the second end of the antenna, and a meandering electrode disposed on a major surface of the bottom fold portion. The antenna includes a plurality of substantially concentric loops including a plurality of middle loops disposed between an innermost loop and an outermost loop. A radius of curvature of each middle loop along at least 95% of an entire length of the middle loop is greater than about 0.1 mm and less than about 4 mm. The meandering electrode has first and second electrode ends making electrical connections with the respective first and second terminals.

In some aspects of the present description, a radio frequency identification tag is provided that includes a stretchable substrate having opposite major top and bottom surfaces, an antenna having a plurality of substantially concentric loops disposed on the major top surface and including an innermost loop and an outermost loop, a first terminal disposed within the innermost loop and in electrical communication with a first end of the antenna, a second terminal disposed outside the outermost loop and in electrical communication with a second end of the antenna, and a meandering electrode disposed on the major bottom surface. A radius of curvature of the antenna along at least 95% of each loop of the antenna is greater than about 0.1 mm and less than about 4 mm. The meandering electrode has first and second electrode ends making crimp connections with the respective first and second terminals.

BRIEF DESCRIPTION OF THE DRAWINGS

FIG. 1D is a top view of an RFID antenna with a dielectric layer.

DETAILED DESCRIPTION

Figure 1A:
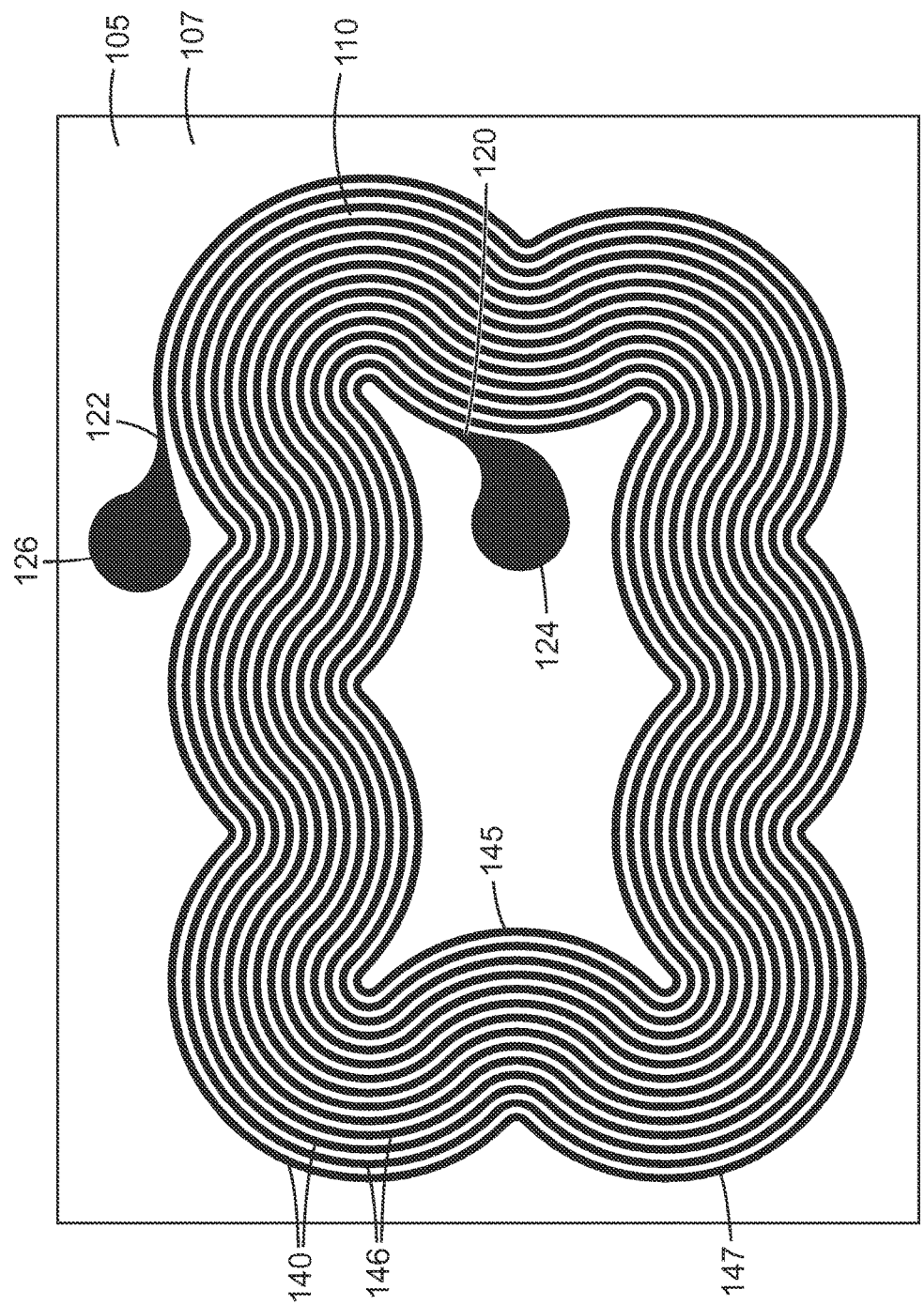
FIGS. 1A-1C are top views of an RFID tag.

In the following description, reference is made to the accompanying drawings that forms a part hereof and in which are shown by way of illustration. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g. 1 to 5 includes 1, 1.5, 2, 2.75, 3, 3.80, 4, and 5) and any range within that range.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

Spatially related terms, including but not limited to, "lower," "upper," "beneath," "below," "above," and "on top," if used herein, are utilized for ease of description to describe spatial relationships of an element(s) to another. Such spatially related terms encompass different orientations of the device in use or operation in addition to the particular orientations depicted in the figures and described herein. For example, if an object depicted in the figures is turned over or flipped over, portions previously described as below or beneath other elements would then be above those other elements.

As used herein, when an element, component or layer for example is described as forming a "coincident interface" with, or being "on" "connected to," "coupled with" or "in contact with" another element, component or layer, it can be directly on, directly connected to, directly coupled with, in direct contact with, or intervening elements, components or layers may be on, connected, coupled or in contact with the particular element, component or layer, for example. When an element, component or layer for example is referred to as being "directly on," "directly connected to," "directly coupled with," or "directly in contact with" another element, there are no intervening elements, components or layers for example.

As used herein, layers, components, or elements may be described as being adjacent one another. Layers, components, or elements can be adjacent one another by being in direct contact, by being connected through one or more other components, or by being held next to one another or attached to one another. Layers, components, or elements that are in direct contact may be described as being immediately adjacent.

It is sometimes desired to attach electronics to human skin. Such electronics includes radio frequency identification (RFID) tags that can be used to authenticate a user. For example, a person could attach an RFID tag to their skin which could then automatically provide the necessary authentication via near field communication (NFC) to an NFC-enabled computer, tablet, phone, or the like that the person may use. RFID tags may include an antenna that includes a coil. When incorporated onto a flexible substrate attached to skin, conventional coil designs may break at stress concentration points along the coil. For example, a conventional coil may include substantially rectangular arrangements of copper traces which can have high stress concentration near the corners when stretched. According to the present description, RFID tags are provided that can stretch and conform to human skin without breaking. Such an RFID tag may include an antenna having a spiral geometry as described herein which allows the antenna to flex and stretch without being prone to damage.

FIG. 1A shows a top view of an RFID assembly that includes a stretchable substrate 105 having a major top surface 107 and an opposite major bottom surface, an antenna 110 having a plurality of substantially concentric loops 140 disposed on the major top surface 107 and including an innermost loop 145, a plurality of middle loops 146 and an outermost loop 147, a first terminal 124 disposed within the innermost loop 145 and in electrical communication with a first end 120 of the antenna 110, a second terminal 126 disposed outside the outermost loop 147 and in electrical communication with a second end 122 of the antenna 110.

A radio frequency identification (RFID) tag may be made using antenna 110 by printing a dielectric layer on the antenna 110 leaving at least portions of the first and second terminals 124 and 126 exposed. An electrode may be applied which electrically connects the first and second terminals directly or indirectly through a pad portion for mounting an integrated circuit. The electrode may be formed by printing an electrically conductive ink on and between the exposed portions of the first and second terminals 124 and 126. The electrically conductive ink may electrically connect the first and second terminals. The conductive ink may include powered or flaked silver or the like in a binder. The dielectric layer prevents the conductive ink from contacting any of the loops of the antenna.

Figure 1B:
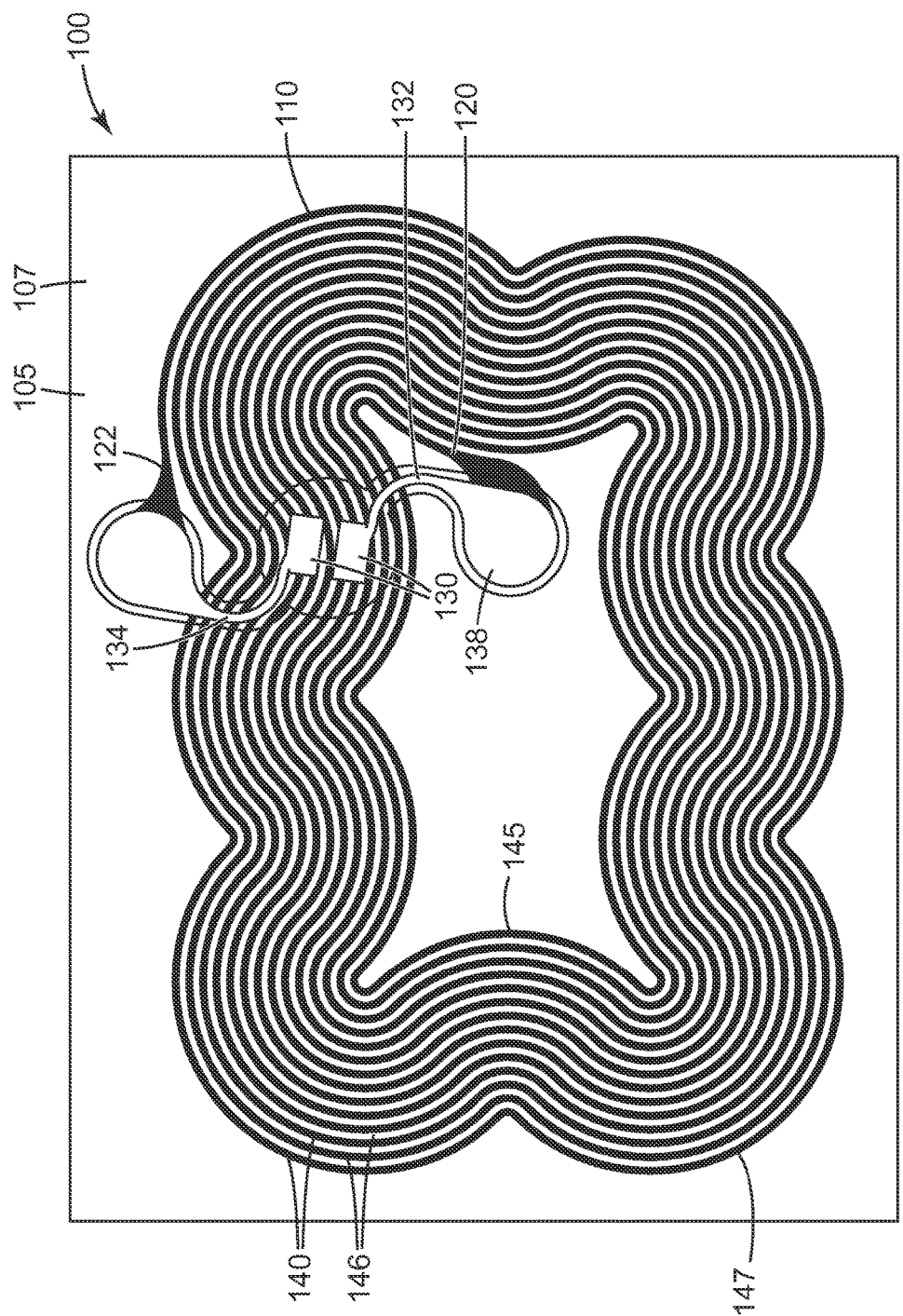

FIG. 1B illustrates an RFID tag that includes the antenna 110 of FIG. 1A. An electrode 138 connects the first terminal 124 and the second terminal 126. In the illustrated embodiment, electrode 138 includes pad portions 130 for connecting an integrated circuit. Electrode 138 includes circuits 132 and 134 which may be formed from electrically conductive ink.

Figure 1C:
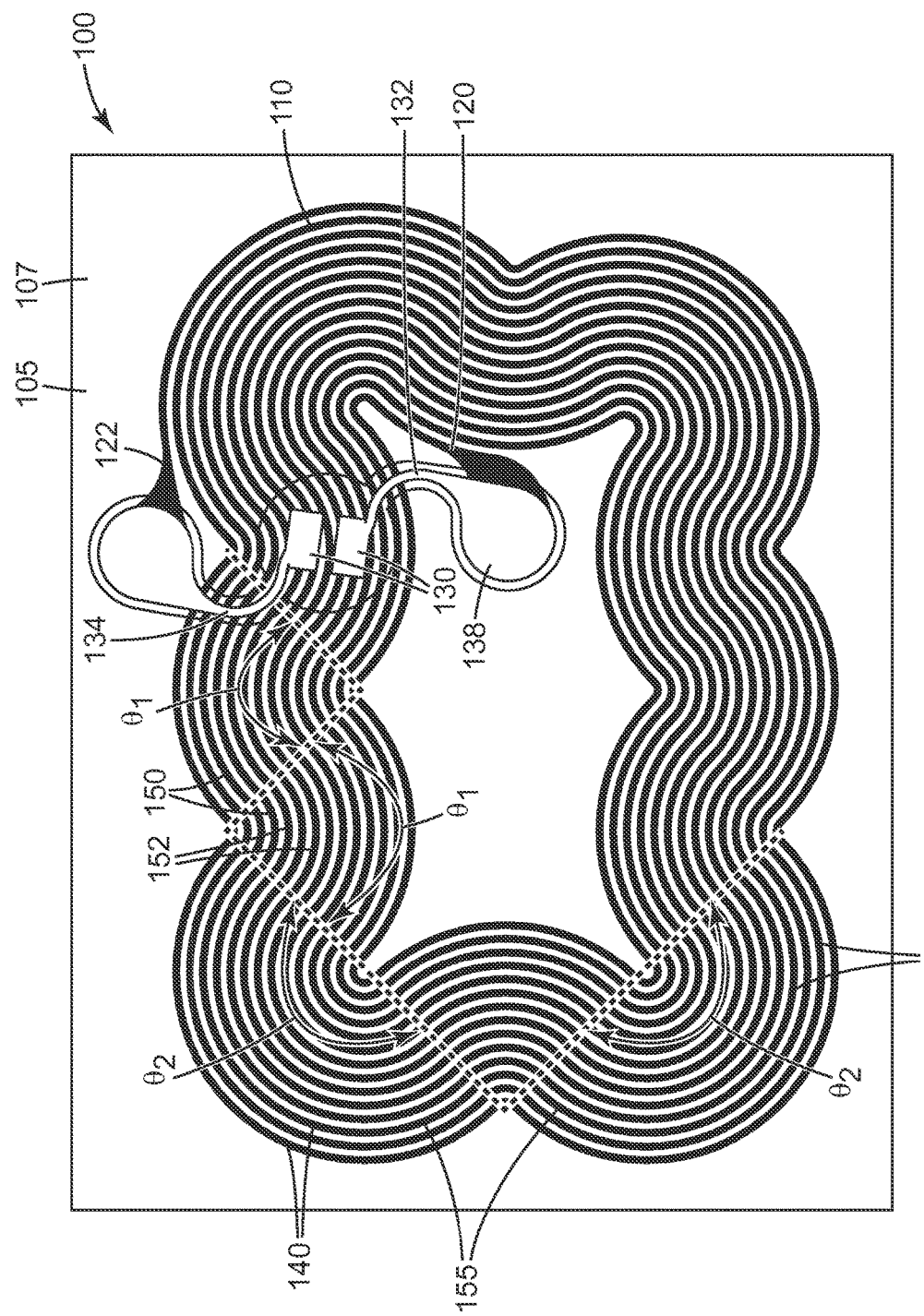

FIG. 1C shows the RFID tag 100 of FIG. 1B illustrating one or more first zones 150 and one or more second zones 155 formed by the substantially concentric loops 140. Each first zone 150 includes a plurality of concentric first arcs 152. In some embodiments, each first arc in the one or more first zones has a same first arc angle $\theta_1$ in a range from about 60 degrees to about 120 degrees, or in a range from about 70 degrees to about 110 degrees, or in a range from about 80 degrees to about 100 degrees. Each second zone 155 includes a plurality of concentric second arcs 157. In some embodiments, each second arc in the one or more second zones has a same second arc angle $\theta_2$ in a range from about 150 degrees to about 210 degrees or in a range from about 160 degrees to about 200 degrees or in a range of about 170 degrees to about 190 degrees. In some embodiments, the first arc angle $\theta_1$ is about 90 degrees and the second arc angle $\theta_2$ is about 180 degrees. Antennas useful with the RFID tags of the present description are also described in commonly assigned U.S. Prov. Pat. App. Ser. No. 62/031,603, entitled "RFID TAG ON FLEXIBLE SUBSTRATE", filed on an even date herewith, and hereby incorporated herein by reference in its entirety.

Antennas suitable for use in RFID tags of the present description can be made by laminating a metallic foil onto a substrate. For example, a copper foil or an aluminum foil and a polymer film can be heat laminated together. Suitable polymer films include elastomeric polyurethane, co-polyester, or polyether block amide films. In other embodiments, a material is extruded directly onto a metallic foil forming a substrate layer attached to the metallic foil. For example, a polyurethane resin may be extruded onto a copper foil. In other embodiments, a material, such as a urethane, is solvent coated onto a metallic foil. Once the metallic foil has been attached to a substrate or once a substrate layer has been formed on the metallic foil, the metallic foil may then be patterned using conventional wet etching techniques to produce a spiral antenna disposed on a major surface of the substrate. The metallic foil may have a thickness in the range of about 10 microns to about 30 microns or to about 50 microns, and the substrate may have a thickness in the range of about 10 microns to about 50 microns, or to about 100 microns, or to about 125 microns.

In some embodiments, a dielectric layer may be deposited onto antenna 110 to separate antenna 110 from electrode 138. This is illustrated in FIG. 1D where dielectric layer 132 covers an antenna leaving a portion 125 of first terminal 124 exposed and leaving a portion 127 of second terminal 126 exposed. An electrode may connect first and second exposed portions 125 and 127.

Figure 2:
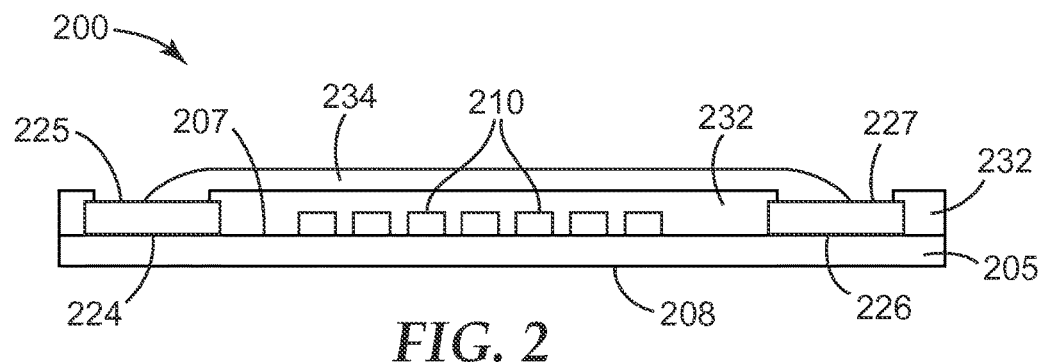
FIG. 2 is a schematic cross-sectional view of a portion of an RFID tag.

FIG. 2 is a cross-sectional view of a portion of an RFID tag 200. RFID tag 200 includes a substrate 205 having major top surface 207 and major bottom surface 208, antenna 210 disposed on major top surface 207, first terminal 224 and second terminal 226. Dielectric layer 232 is disposed on the antenna 210 leaving at least a portion 225 of first terminal 224 exposed and leaving at least a portion 227 of second terminal 226 exposed. FIG. 2 shows the portion of antenna 210 that included in the cross-section between first terminal 224 and second terminal 226. Antenna 210 also includes a portion, which is not included in FIG. 2, that is not disposed between first terminal 224 and second terminal 226.

Dielectric layer 232 may include a radiation-cured material which may be an ultraviolet (UV)-cured material. Dielectric layer 232 may be printed using one or more of ink jet printing, screen printing, gravure printing, and flexographic printing. Dielectric layer 232 may be about 2 microns to about 50 microns thick or may be about 3 microns to about 30 microns thick. Electrode 234 electrically connects the first terminal 224 and the second terminal 226. Electrode 234 may be formed by printing an electrically conductive ink on and between the exposed portions 225 and 227 of the first and second terminals 224 and 226. The dielectric layer 232 prevents the electrically conductive ink from contacting any of the loops of the antenna. In some embodiments, electrode 234 is formed by printing an electrically conductive ink that includes metallic particles. Suitable metallic particles include metallic flakes, such as silver flakes, and metallic nanoparticles, such as silver nanoparticles and copper nanoparticles. In some embodiments, the electrically conductive ink includes carbon particles which may be carbon nanoparticles. The electrically conducing ink may be printed using one or more of ink jet printing, screen printing, gravure printing, and flexographic printing.

Figure 3:
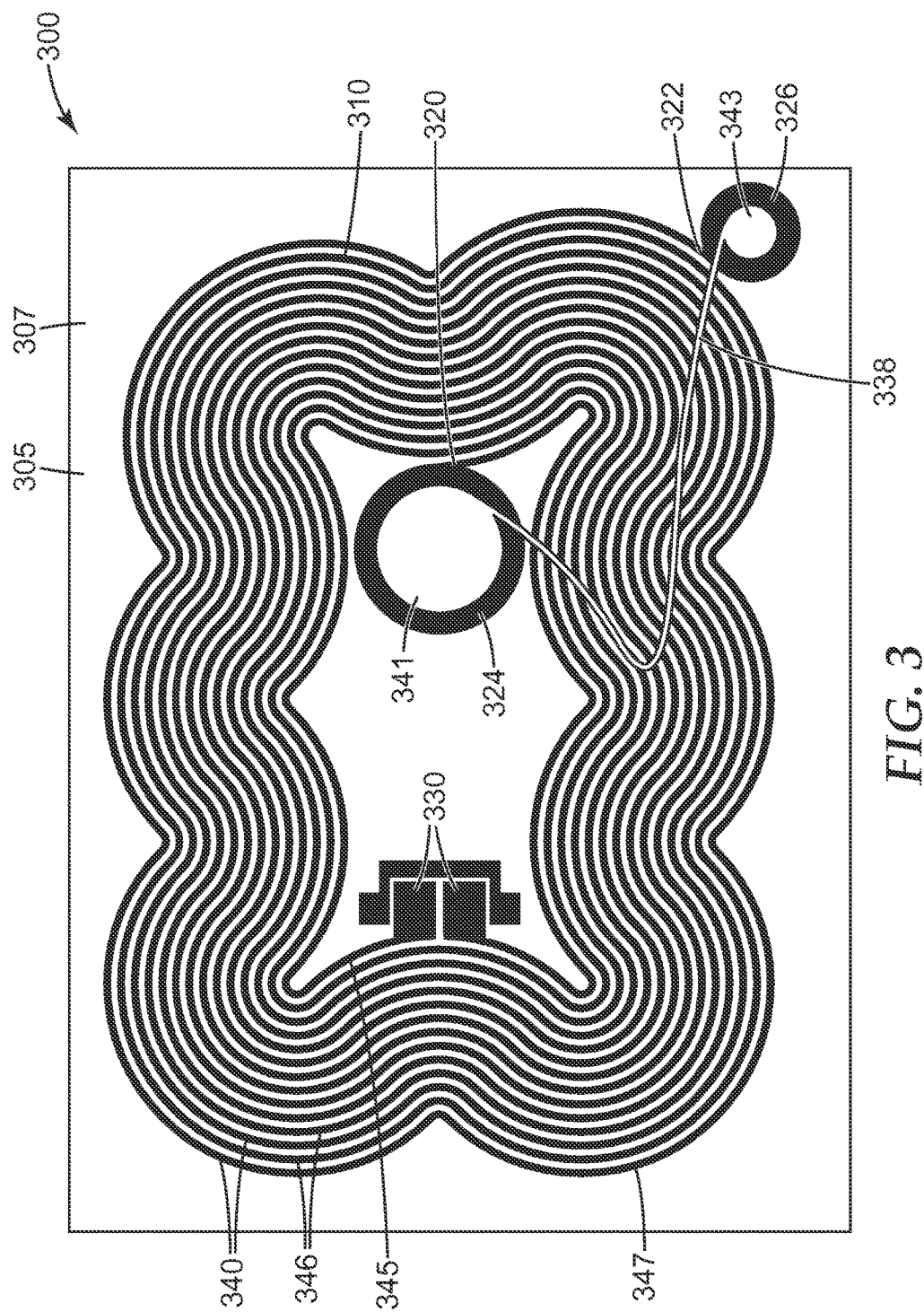
FIG. 3 is a top view of an RFID tag.

FIG. 3 shows an RFID tag 300 that includes a flexible substrate 305 having a top surface 307 and an opposing bottom surface, an antenna 310 having a spiral form disposed on the top surface 307 of the substrate 305 and having a first end 320 and a second end 322, a first terminal 324 disposed at and in electrical communication with the first end 320 of the antenna 310, a second terminal 326 disposed at and in electrical communication with the second end 322 of the antenna, and a pad portion 330 included along the length of the antenna 310 between the first end 320 and the second end 322 for mounting an integrated circuit. Antenna 310 includes a plurality of loops 340 which include an innermost loop 345, a plurality of middle loops 346, and an outermost loop 347. RFID tag 300 includes electrode 338 having a first end 341 attached at first terminal 324 and a second end 343 attached at second terminal 326. Electrode 338 may be a wire that connects the first and second terminals 324 and 326 and a dielectric layer may be included between antenna 310 and electrode 338 in order to prevent electrode 338 from contacting any of the loops of antenna 310.

Figure 4:
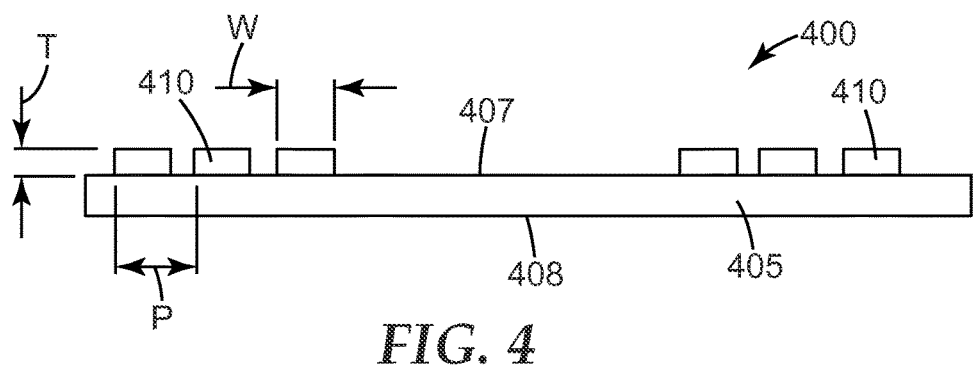
FIG. 4 is a schematic cross-sectional view of an RFID tag.

FIG. 4 is a schematic cross-sectional view of a portion of RFID tag 400 including substrate 405 having major top surface 407, major bottom surface 408, and antenna 410 disposed on the major top surface 407. The antenna 410 may have any of the antenna geometries described elsewhere and may include a metal spiral trace that forms a plurality of substantially concentric loops. The antenna 410 may have a thickness T along a direction perpendicular to the stretchable substrate 405 that may be in a range from about 2 microns, or about 10 microns, to about 30 microns, or about 50 microns, and a width W that that may be in a range from about 10 microns, or about 50 microns, to about 300 microns, or about 500 microns. The plurality of substantially concentric loops of the antenna 410 may form a pitch P which may be in a range from about 30 microns, or about 75 microns, or about 150 microns, to about 400 microns, or to about 800 microns.

For any of the antennas of the present description, a radius of curvature of the antenna along at least 90% or at least 95% of each loop of the antenna may be greater than about 0.1 mm and less than about 4 mm or less than about 5 mm or less than about 10 mm. In some embodiments, a radius of curvature of the antenna along at least 95% or at least 98% of each loop of the antenna is greater than about 0.1 mm and less than about 5 mm. In some embodiments, the antenna may include a plurality of substantially concentric loops that include a plurality of middle loops disposed between an innermost loop and an outermost loop. In some embodiments, a radius of curvature of each middle loop along at least 95% or at least 98% of an entire middle loop is greater than about 0.1 mm and less than about 4 mm or less than about 5 mm.

Figure 5:
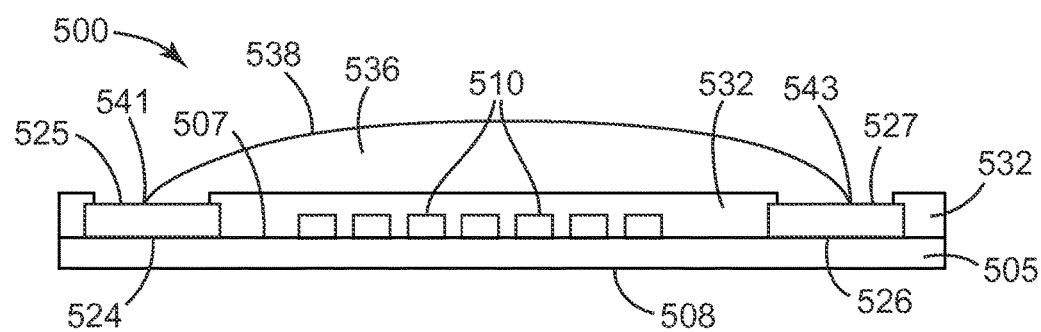
FIG. 5 is a schematic cross-sectional view of a portion of an RFID tag.

FIG. 5 is a cross-sectional view of a portion of an RFID tag 500 including a stretchable substrate 505 having major top surface 507, opposite major bottom surface 508, an antenna 510 disposed on the major top surface 507, a first terminal 524, a second terminal 526, and a dielectric layer 532 printed on the antenna 510 and leaving at least a portion 525 of first terminal 524 exposed and at least a portion 527 of second terminal 526 exposed. RFID tag 500 also includes an electrically conductive wire 538 having a first end 541 attached to and making electrical connection with the first terminal 524, and a second end 543 attached to and making electrical connection with the second terminal 526. Electrical connections can be made using any technique such as attachment with a conductive adhesive or paste or through crimping. A gap 536 is formed between the dielectric layer 532 and the wire 538. Gap 536 may be an air gap. The antenna 510 may have a plurality of substantially concentric loops which may include an innermost loop and an outermost loop as described elsewhere. A radius of curvature of the antenna 510 along at least 95% of each loop of the antenna may be greater than about 0.1 mm and less than about 4 mm and may have other geometries as described elsewhere. The first terminal 524 may be disposed within the innermost loop and may be in electrical communication with a first end of the antenna while the second terminal 526 may be disposed outside the outermost loop and in electrical communication with a second end of the antenna 510. The dielectric layer 532 prevents the wire 538 from contacting any of the loops of the antenna 510.

Figure 6:
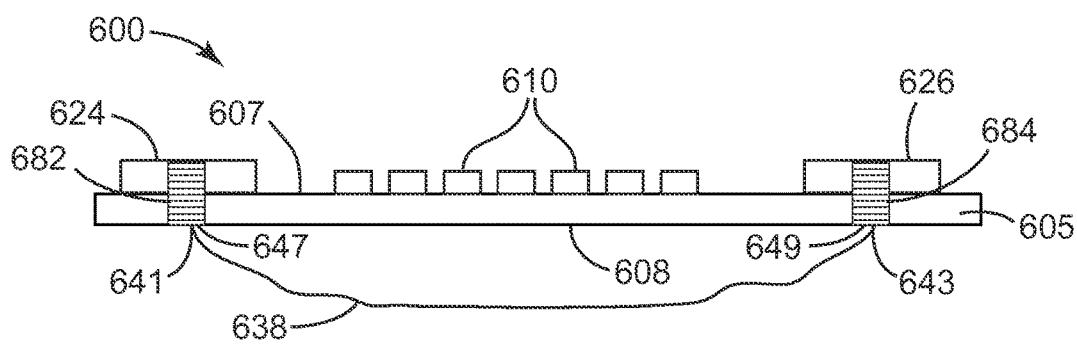
FIG. 6 is a schematic cross-sectional view of a portion of an RFID tag.

FIG. 6 shows RFID tag 600 having a stretchable substrate 605 having major top surface 607 and opposite major bottom surface 608, an antenna 610 disposed on major top surface 607, a first terminal 624 disposed on the major top surface 607, and a second terminal 626 disposed on the major top surface 607. Antenna 610 may have a geometry as described elsewhere. For example, antenna 610 may have a spiral form and a radius of curvature of the antenna along at least 90% or 95% or 98% of an entire length of the antenna between first and second ends of the antenna may be greater than about 0.1 mm and less than about 4 mm or less than about 5 mm. In some embodiments, antenna 610 may include a plurality of substantially concentric loops that include a plurality of middle loops disposed between an innermost loop and an outermost loop. In some embodiments, a radius of curvature of each middle loop along at least 95% or at least 98% of an entire middle loop is greater than about 0.1 mm and less than about 4 mm or less than about 5 mm. First terminal 624 is in direct electrical communication with the first end of antenna 610 and second terminal 626 is in direct electrical communication with the second end of antenna 610. RFID tag 600 includes a first attachment area 647 on major bottom surface 608 corresponding to and aligned with the first terminal 624, and includes a second attachment area 649 on major bottom surface 608 corresponding to and aligned with the second terminal 626. RFID tag 600 further includes a conductive wire 638 having a first end 641 attached to first attachment area 647 and making a crimp connection (represented schematically with crimped region 682) with first terminal 624. Conductive wire 638 also has a second end 643 attached to second attachment area 649 and making a crimp connection (represented schematically with crimped region 684) with second terminal 626.

Crimp connections may be performed using a heated crimping process. A heated tool can be used to melt through a substrate layer or substrate layers and then a crimp tool can be used to provide metal to metal contact through the melted substrate layer or substrate layers. Alternatively, the crimp tool itself may be heated in order to melt through any substrate layers and improve metal to metal contact in the crimped connection.

FIGS. 7A-7D are cross-sectional views of a portion of an RFID antenna assembly 711 and a connector 739 that can be crimped or otherwise electrically connected together to form RFID tags. RFID antenna assembly 711 includes first substrate 705 having major top surface 707 and major bottom surface 708, antenna 710 disposed on major top surface 707, first terminal 724 disposed on major top surface 707, and second terminal 726 disposed on major top surface 707. Connector 739 includes second substrate 755 having major top surface 757 and opposite major bottom surface 758, and meandering electrode 738 including first end 741 and second end 743. FIGS. 7A-7D show the portion of antenna 710 that is included in the cross-section between first terminal 724 and second terminal 726. Antenna 710 also includes a portion, which is not included in FIGS. 7A-7D, that is not disposed between first terminal 724 and second terminal 726.

Figure 7A:
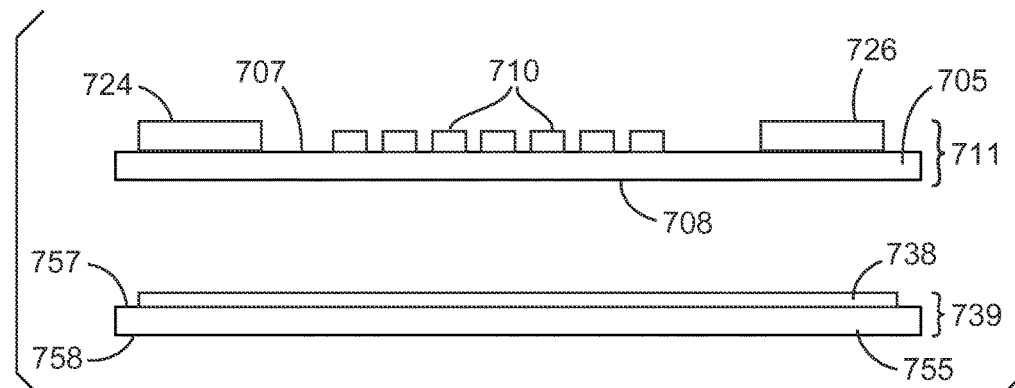
FIGS. 7A-7D are cross-sectional views of a portion of an RFID antenna assembly and a connector.
Figure 7B:
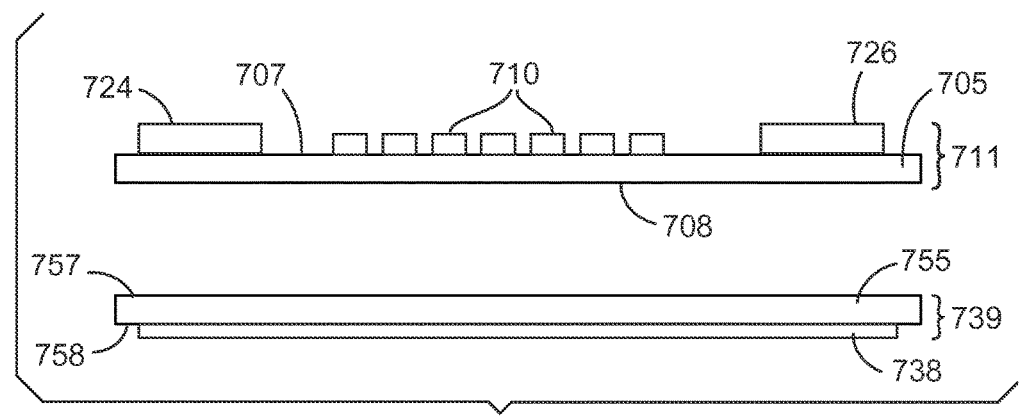
Figure 7C:
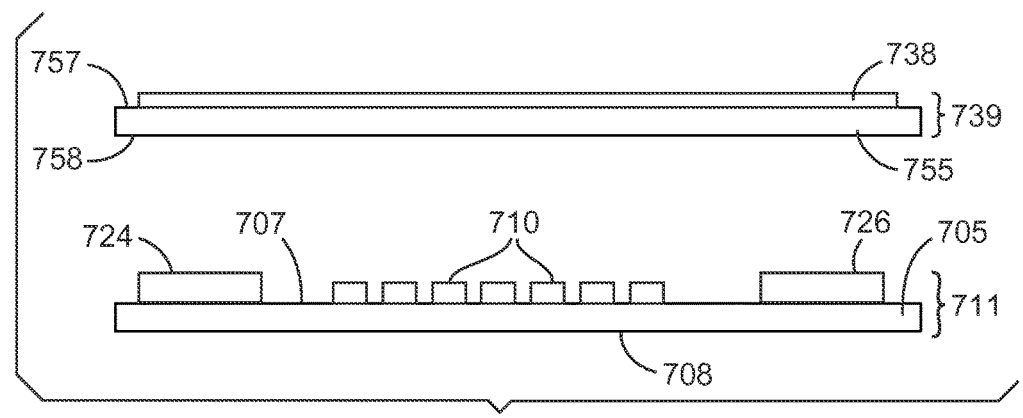
Figure 7D:
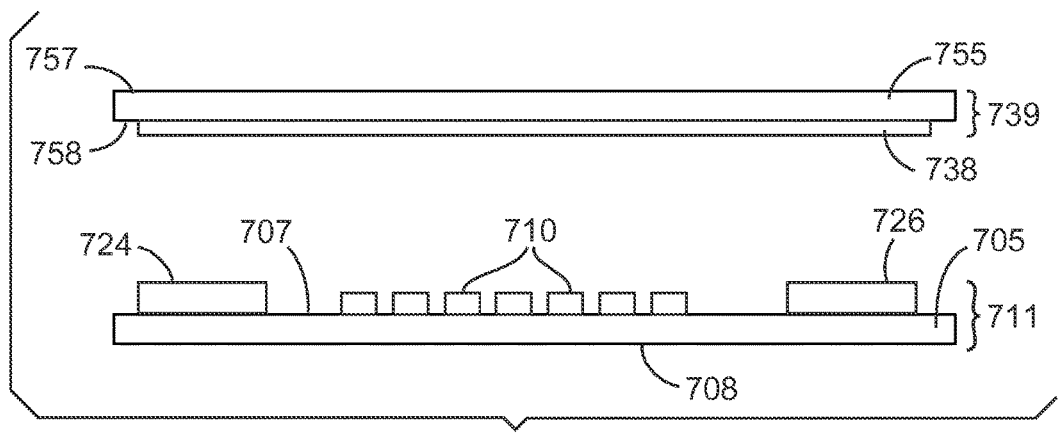

In the embodiment illustrated in FIG. 7A, meandering electrode 738 is disposed on the major top surface 757 of substrate 755 and major top surface 757 faces major bottom surface 708 of substrate 705. FIGS. 7B-7D illustrate alternative arrangements of RFID antenna assembly 711 and connector 739 prior to crimping. In the embodiments illustrated in FIGS. 7B and 7D, meandering electrode 738 is disposed on the major bottom surface 758. In the embodiment illustrated in FIG. 7C, meandering electrode 738 is disposed on the major top surface 757 of substrate 755 and major bottom surface 758 faces major top surface 707 of substrate 705. In the embodiments illustrated in FIGS. 7A and 7B, connector 739 is disposed adjacent major bottom surface 708 opposite major top surface 707 and in the embodiments illustrated in FIGS. 7C and 7D, connector 739 is disposed adjacent major top surface 707 opposite major bottom surface 708. In the embodiment illustrated in FIGS.

7A and 7B, major top surface 757 of substrate 755 faces major bottom surface 708 of substrate 705. In the embodiment illustrated in FIGS. 7C and 7D, major bottom surface 758 of substrate 755 faces major top surface 707 of substrate 705.

In some embodiments, second substrate 755 is stretchable and in some embodiments second substrate 755 is not stretchable. In some embodiments, second substrate 755 includes polyimide. For example, second substrate 755 may be a polyimide film.

Figure 7E:
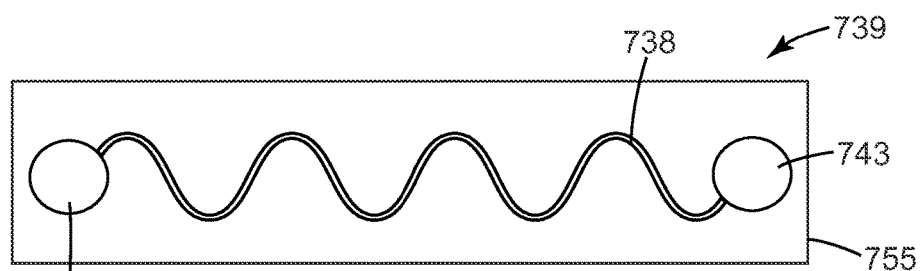
FIG. 7E is a top view of a connector.

FIG. 7E shows a top view of connector 739 where meandering electrode 738 is disposed on a major surface of second substrate 755. Meandering electrode 738 may have any suitable shape. In some embodiments, meandering electrode 738 has a substantially sinusoidal shape. In some embodiments, a radius of curvature of the meandering electrode 738 along at least 90% or at least 95% or at least 98% of an entire length between first end 741 and second end 743 is greater than about 0.1 mm and less than about 10 mm.

In the embodiment illustrated in FIG. 7D, a dielectric layer may be disposed between antenna 710 and meandering electrode 738 to prevent meandering electrode 738 from contacting antenna 710. This may be done by printing a dielectric layer onto antenna 710 leaving openings which exposes at least a portion of first terminal 724 and at least a portion of second terminal 726 as described elsewhere. In the embodiment illustrated in FIG. 7D, meandering electrode 738 may be attached to first terminal 724 and second terminal 726 through a conductive paste or adhesive or may be attached through crimping.

Figure 7F:
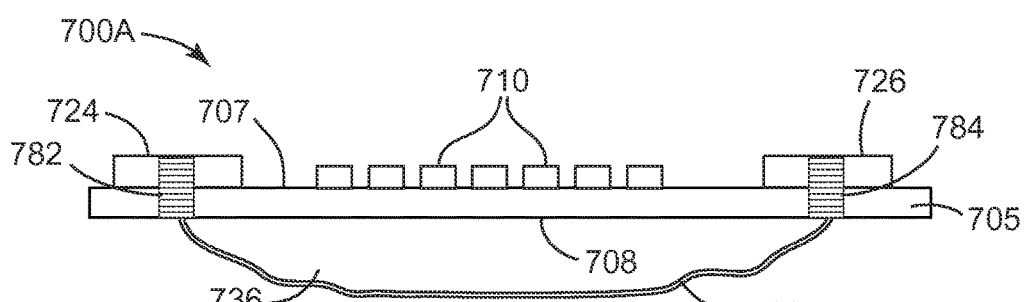
FIGS. 7F-7G are schematic cross-sectional views of portions of RFID tags made using the RFID antenna assemblies and connectors of FIGS. 7A-7E.
Figure 7G:
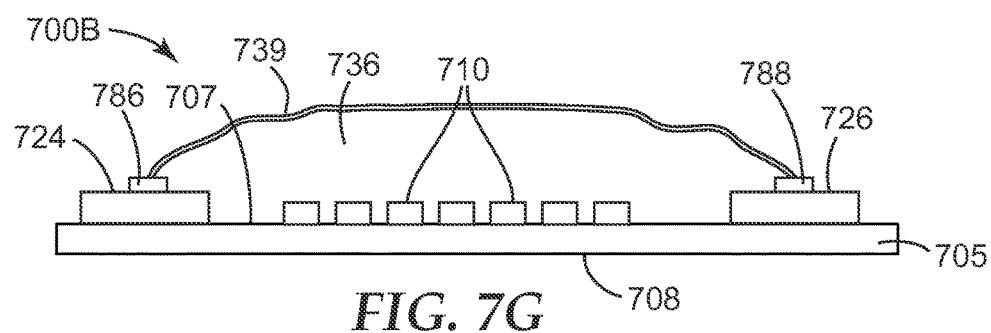

FIG. 7F shows a portion of RFID tag 700A formed by electrically connecting the RFID antenna assembly 711 and a connector 739 arranged as indicated in FIG. 7A or 7B. FIG. 7G shows a portion of RFID tag 700B formed by electrically connecting the RFID antenna assembly 711 and a connector 739 arranged as indicated in FIG. 7C or 7D. RFID tags 700A and 700B include a stretchable substrate 705 having major top surface 707 and major bottom surface 708, antenna 710 disposed on major top surface 707, first terminal 724 and second terminal 726. Antenna 710 has a spiral form and has first and second ends. Antenna 710 may have any of the spiral geometries discussed elsewhere. First terminal 724 is disposed on the major top surface 707 and is in electrical communication with the first end of antenna 710. Second terminal 726 is disposed on the major top surface 707 and is in electrical communication with the second end of antenna 710. Connector 739 includes a second substrate 755, which is discrete from first stretchable substrate 705, having opposite major top and bottom surfaces 757 and 758 with one of the major top and bottom surfaces 757 and 758 of the second substrate 755 facing one of the major top and bottom surfaces 707 and 708 of the first stretchable substrate 705 as illustrated in FIGS. 7A-7D. Connector 739 also includes a meandering electrode 738 disposed on one of the major top and bottom surfaces 757 and 758 of the second substrate 755.

The meandering electrode 738 has first and second electrode ends 741 and 743. In forming RFID tags 700A and 700B from the assemblies illustrated in FIGS. 7A-7E, connector 739 may be placed such that first and second electrode ends 741 and 743 are in registration with first and second terminals 724 and 726. Crimping then results in the first end 741 of the meandering electrode making electrical connection with first terminal 724 through crimped region 782 and the second end 743 of the meandering electrode making electrical connection with second terminal 726 through crimped region 784 as schematically illustrated in FIG. 7F. Alternatively, in some embodiments, electrical connection between meandering electrode 738 and first and second terminals 724 and 726 may be established through use of a conductive adhesive or paste. This is illustrated in FIG. 7G where the meandering electrode makes electrical connection with first terminal 724 through conductive adhesive or paste 786 and the second end 743 of the meandering electrode makes electrical connection with second terminal 726 through conductive adhesive or paste 788.

In the embodiments illustrated in FIGS. 7F-7G, RFID tags 700A and 700B include a gap 736 between the first stretchable substrate and the second substrate 755 of connector 739. In some embodiments, gap 736 is an air gap.

In some embodiments, second substrate 755 is disposed between antenna 710 and meandering electrode 738 as illustrated in FIGS. 7B and 7C. In some embodiments, first end 741 of meandering electrode 738 makes a crimp connection with first terminal 724 and second end 743 of meandering electrode 738 makes a crimp connection with second terminal 726. In some embodiments, the first stretchable substrate 705 is disposed between the antenna 710 and the meandering electrode 738 as illustrated in FIG. 7B. In some embodiments, the first stretchable substrate 705 is not disposed between the antenna 710 and the meandering electrode 738 as illustrated in FIG. 7C.

In some embodiments, second substrate 755 is not disposed between antenna 710 and meandering electrode 738. This is illustrated in FIGS. 7A and 7D. In some embodiments, the first stretchable substrate 705 is disposed between the antenna 710 and the meandering electrode 738 as illustrated in FIG. 7A. In some embodiments, the first stretchable substrate 705 is not disposed between the antenna 710 and the meandering electrode 738 as illustrated in FIG. 7D. In some embodiments, the first end 741 of meandering electrode 738 directly contacts first terminal 724 and second end 743 of meandering electrode 738 directly contacts second terminal 726. In some embodiments, the first end 741 of meandering electrode 738 makes electrical connection with first terminal 724 by crimping or by using a conductive paste or adhesive as described elsewhere and second end 743 of meandering electrode 738 makes electrical connection with second terminal 726 by crimping or by using a conductive paste or adhesive as described elsewhere.

Figure 8:
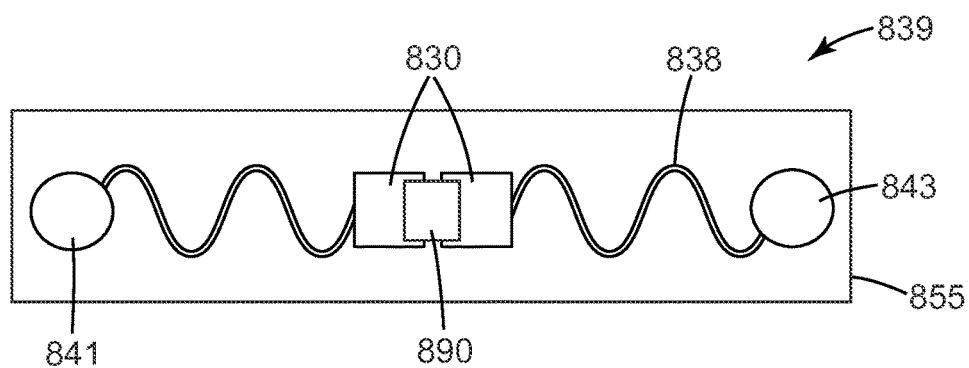
FIG. 8 is a top view of a connector.

In some embodiments, an RFID tag may include an integrated circuit disposed on the major top surface 757 or major bottom surface 758 of second substrate 755 and in electrical communication with the meandering electrode. In some embodiments, the meandering electrode includes pad portions in electrical communication with the electrode for mounting the integrated circuit. This is illustrated in FIG. 8 which shows connector 839 including meandering electrode 838 disposed on a major top or bottom surface of substrate 855. Meandering electrode 838 includes first end 841, second end 843 and pad portion 830. Integrated circuit 890 is disposed on pad portion 830. In some embodiments, except for the pad portion 830, a radius of curvature of the meandering electrode 838 along at least 90% or 95% or 98% of the length between first end 841 and second end 843 is greater than about 0.1 mm and less than about 10 mm.

FIGS. 9A-9D show portions of RFID assemblies having a stretchable substrate 905 folded along a fold line 972 to form top fold portion 906 and bottom fold portion 956. Top fold portion 906 includes major top surface 907 and opposing major bottom surface 908. Bottom fold portion 956 includes major top surface 957 and opposing major bottom surface 958. The RFID assemblies includes antenna 910, first terminal 924 and second terminal 926 disposed on a major surface of top fold portion 906. FIGS. 9A-9D show the portion of antenna 910 that is included in the cross-section between first terminal 924 and second terminal 926. Antenna 910 also includes a portion, which is not included in FIGS. 9A-9D, that is not disposed between first terminal 924 and second terminal 926.

Figure 9A:
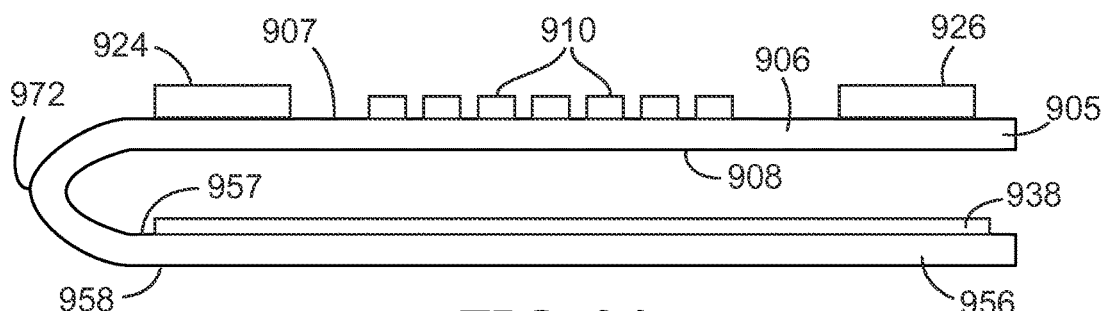
FIGS. 9A-9D are cross-sectional views of portions of RFID assemblies.
Figure 9B:
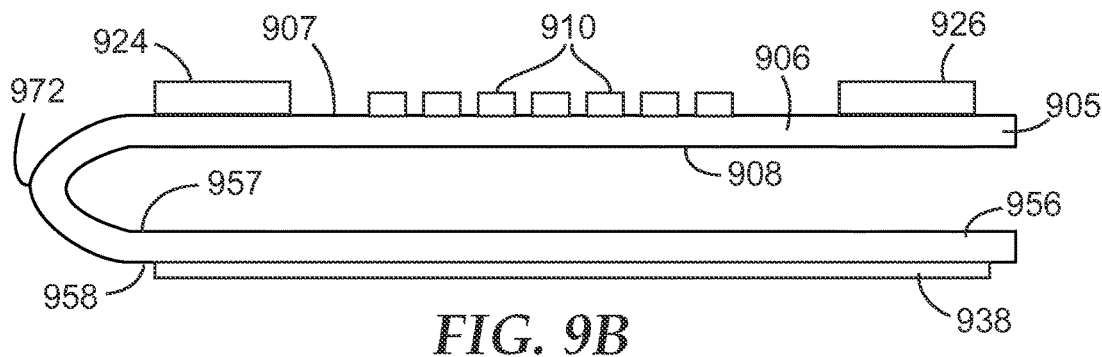
Figure 9C:
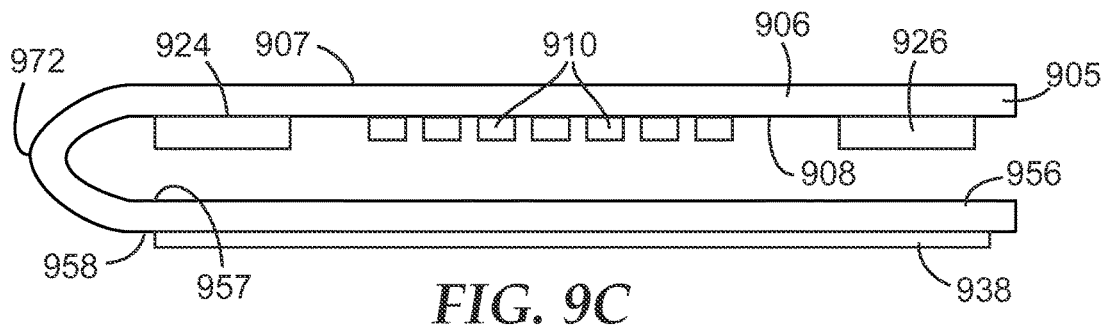

In the embodiments illustrated in FIGS. 9A-9B, antenna 910, first terminal 924 and second terminal 926 are disposed on major top surface 907. In the embodiments illustrated in FIGS. 9C-9D, antenna 910, first terminal 924 and second terminal 926 are disposed on major bottom surface 908. The RFID assemblies include meandering electrode 938 disposed on a major surface of the bottom fold portion 956. In the embodiments illustrated in FIGS. 9A and 9D, meandering electrode 938 is disposed on major top surface 957. In the embodiments illustrated in FIGS. 9B-9C, meandering electrode 938 is disposed on major bottom surface 958.

Figure 9D:
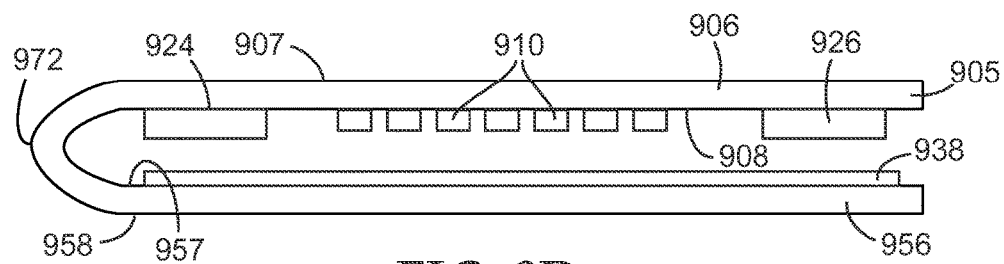

In the embodiment illustrated in FIG. 9D, a dielectric layer may be disposed between antenna 910 and meandering electrode 938 to prevent meandering electrode 938 from contacting antenna 910. This may be done by printing a dielectric layer onto antenna 910 leaving openings which exposes at least a portion of first terminal 924 and at least a portion of second terminal 926 as described elsewhere.

Figure 10:
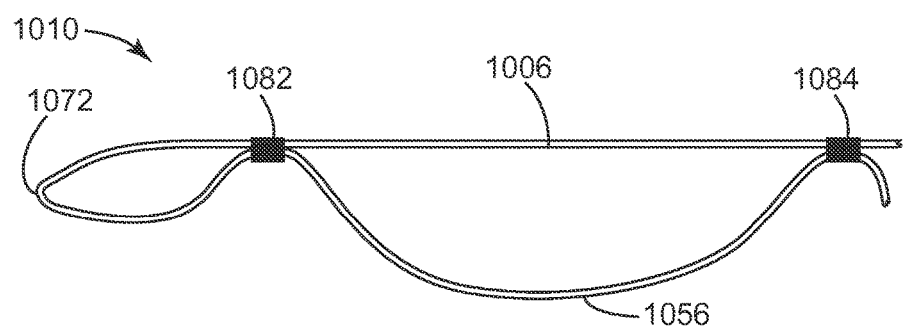
FIG. 10 is a schematic side view of a portion of an RFID tag.

The RFID assemblies of FIGS. 9A-9D may be crimped or otherwise electrically connected so that first and second ends of meandering electrode 938 make electrical connections with the respective first and second terminals 924 and 926. This is schematically illustrated in FIG. 10 which shows RFID tag 1010 including top fold portion 1006 and bottom fold portion 1056. A first attachment region 1082 is indicated where an attachment between an electrode disposed on a major surface of bottom fold portion 1056 and a first terminal disposed on a major surface of top fold portion 1006 is established. A second attachment region 1084 is indicated where an attachment between an electrode disposed on a major surface of bottom fold portion 1056 and a second terminal disposed on a major surface of top fold portion 1006 is established. Attachment regions 1082 and 1084 may be formed through crimping. Alternatively, in embodiments where meandering electrode 938 faces first and second terminals 924 and 926 with no intervening substrate, attachment regions 1082 and 1084 may be formed through the use of a conductive paste or adhesive.

Figure 11:
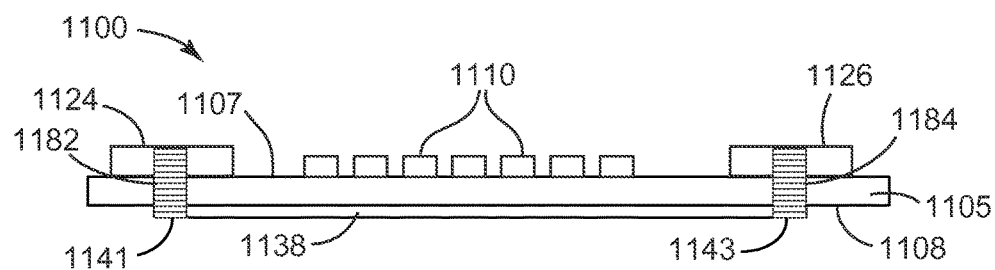
FIG. 11 is a schematic side view of a portion of an RFID tag.

FIG. 11 is a schematic cross-sectional view of a portion of RFID tag 1100 which includes a stretchable substrate 1105 having major top surface 1107 and opposing major bottom surface 1108, an antenna 1110, a first terminal 1124, a second terminal 1126, and a meandering electrode 1138. Antenna 1110 may have any of the geometries discussed elsewhere. For example, antenna 1110 may include a plurality of substantially concentric loops disposed on the major top surface 1107 and may include an innermost loop and an outermost loop, and a radius of curvature of antenna 1110 along at least 95% of each loop of the antenna 1110 may be greater than about 0.1 mm and less than about 4 mm. First terminal 1124 is disposed within the innermost loop and is in electrical communication with a first end of the antenna. Second terminal 1126 is disposed outside the outermost loop and is in electrical communication with a second end of the antenna. Meandering electrode 1138 is disposed on the major bottom surface 1108 and has first electrode end 1141 and second electrode end 1143. The first electrode end 1141 makes a crimp connection 1182 with first terminal 1124 and the second electrode end 1143 makes a crimp connection 1184 with second terminal 1126. Meandering electrode 1138 may have any of the electrode geometries described elsewhere. For example, meandering electrode 1138 may have a substantially sinusoidal shape or may have a radius of curvature along at least 90% of the length between first and second ends that is greater than about 0.1 mm and less than about 10 mm.

Any of the RFID tags described herein may be attached to skin using a suitable adhesive. Suitable adhesives include hypoallergenic acrylate copolymer bioadhesives such as those described in U.S. Pat. No. 5,088,483 (Heinecke).

The following is a list of exemplary embodiments of the present description.

Item 1. A radio frequency identification tag comprising:
  a stretchable substrate having opposite major top and bottom surfaces;
  an antenna having a plurality of substantially concentric loops disposed on the major top surface and comprising an innermost loop and an outermost loop, a radius of curvature of the antenna along at least 90% of each loop of the antenna being greater than about 0.1 mm and less than about 5 mm;
  a first terminal disposed within the innermost loop and in electrical communication with a first end of the antenna;
  a second terminal disposed outside the outermost loop and in electrical communication with a second end of the antenna;
  a dielectric layer printed on the antenna leaving at least portions of the first and second terminals exposed; and
  an electrically conductive ink printed on and between the exposed portions of the first and second terminals and electrically connecting the first and second terminals, the dielectric layer preventing the conductive ink from contacting any of the loops of the antenna.

Item 2. The radio frequency identification tag of item 1, wherein the stretchable substrate comprises polyurethane.

Item 3. The radio frequency identification tag of item 1, wherein the substantially concentric loops form a plurality of concentric first arcs having a same first arc angle and a plurality of concentric second arcs having a same second arc angle different than the first arc angle.

Item 4. The radio frequency identification tag of item 3, wherein the first arc angle is in a range from about 60 degrees to about 120 degrees.

Item 5. The radio frequency identification tag of item 3, wherein the first arc angle is in a range from about 80 degrees to about 100 degrees.

Item 6. The radio frequency identification tag of item 3, wherein the second arc angle is in a range from about 150 degrees to about 210 degrees.

Item 7. The radio frequency identification tag of item 3, wherein the second arc angle is in a range from about 160 degrees to about 200 degrees.

Item 8. The radio frequency identification tag of item 3, wherein the second arc angle is in a range from about 170 degrees to about 190 degrees.

Item 9. The radio frequency identification tag of item 3, wherein the first arc angle is about 90 degrees and the second arc angle is about 180 degrees.

Item 10. The radio frequency identification tag of item 1, wherein the radius of curvature of the antenna along at least 90% of each loop of the antenna is greater than about 0.1 mm and less than about 4 mm.

Item 11. The radio frequency identification tag of item 1, wherein the radius of curvature of the antenna along at least 95% of each loop of the antenna is greater than about 0.1 mm and less than about 5 mm.

Item 12. The radio frequency identification tag of item 1, wherein the radius of curvature of the antenna along at least 98% of each loop of the antenna is greater than about 0.1 mm and less than about 5 mm.

Item 13. The radio frequency identification tag of item 1, wherein the antenna comprises a metal spiral trace forming the plurality of substantially concentric loops.

Item 14. The radio frequency identification tag of item 1, wherein the antenna has a length between the first and second ends of the antenna, a thickness along a direction perpendicular to the stretchable substrate that is in a range from about 2 microns to about 30 microns, and a width that is in a range from about 50 microns to about 300 microns.

Item 15. The radio frequency identification tag of item 1, wherein the plurality of substantially concentric loops form a pitch in a range from about 150 microns to about 400 microns.

Item 16. The radio frequency identification tag of item 1, wherein the dielectric layer comprises a UV-cured material.

Item 17. The radio frequency identification tag of item 1, wherein the dielectric layer is printed using one or more of ink jet printing, screen printing, gravure printing, and flexographic printing.

Item 18. The radio frequency identification tag of item 1, wherein the dielectric layer is in a range of about 3 microns to about 30 microns thick.

Item 19. The radio frequency identification tag of item 1, wherein the electrically conductive ink comprises metallic particles.

Item 20. The radio frequency identification tag of item 19, wherein the metallic particles comprise silver flakes.

Item 21. The radio frequency identification tag of item 1, wherein the electrically conductive ink is printed using one or more of ink jet printing, screen printing, gravure printing and flexographic printing.

Item 22. A radio frequency identification tag comprising:
  a stretchable substrate having opposite major top and bottom surfaces;
  an antenna having a spiral form disposed on the major top surface, a radius of curvature of the antenna along at least 95% of an entire length of the antenna between first and second ends of the antenna being greater than about 0.1 mm and less than about 4 mm;
  a first terminal disposed on the top surface and in electrical communication with the first end;
  a second terminal disposed on the top surface and in electrical communication with the second end;
  a first attachment area on the major bottom surface corresponding to and aligned with the first terminal;
  a second attachment area on the major bottom surface corresponding to and aligned with the second terminal; and
  a conductive wire having first and second ends attached to the respective first and second attachment areas and making crimp connections with the respective first and second terminals.

Item 23. The radio frequency identification tag of item 22, wherein the antenna comprises a plurality of substantially concentric loops comprising a plurality of middle loops disposed between an innermost loop and an outermost loop, wherein the radius of curvature of each middle loop along at least 98% of an entire length of the middle loop is greater than about 0.1 mm and less than about 4 mm.

Item 24. A radio frequency identification tag comprising:
  a first stretchable substrate having opposite major top and bottom surfaces;
  an antenna having a spiral form disposed on the major top surface and having a length between first and second ends;
  a first terminal disposed on the major top surface and in electrical communication with the first end;
  a second terminal disposed on the major top surface and in electrical communication with the second end;
  a second substrate, discrete from the first stretchable substrate, having opposite major top and bottom surfaces, one of the major top and bottom surfaces of the second substrate facing one of the major top and bottom surfaces of the first stretchable substrate;
  a meandering electrode disposed on one of the major top and bottom surfaces of the second substrate and having first and second electrode ends in registration and making electrical connections with the respective first and second terminals.

Item 25. The radio frequency identification tag of item 24, wherein there is an air gap formed between the first stretchable substrate and the second substrate.

Item 26. The radio frequency identification tag of item 24 further comprising an integrated circuit disposed on the top or bottom surface of the second substrate in electrical communication with the meandering electrode.

Item 27. The radio frequency identification tag of item 24, wherein the antenna comprises a plurality of substantially concentric loops comprising a plurality of middle loops disposed between an innermost loop and an outermost loop, wherein a radius of curvature of each middle loop along at least 95% of an entire length of the middle loop is greater than about 0.1 mm and less than about 4 mm.

Item 28. The radio frequency identification tag of item 24, wherein a radius of curvature of the antenna along at least 95% of an entire length of the antenna between the first and second ends is greater than about 0.1 mm and less than about 10 mm.

Item 29. The radio frequency identification tag of item 24, wherein the meandering electrode comprises a pad portion along the length of the electrode between the first and second electrode ends for mounting an integrated circuit, the pad portion being in electrical communication with the electrode, such that except for the pad portion, a radius of curvature of the electrode along at least 95% of the length of the electrode between the first and second electrode ends is greater than about 0.1 mm and less than about 10 mm.

Item 30. The radio frequency identification tag of item 24, wherein the meandering electrode is substantially sinusoidal.

Item 31. The radio frequency identification tag of item 24, wherein the second substrate is disposed between the antenna and the meandering electrode.

Item 32. The radio frequency identification tag of item 31, wherein the second substrate is stretchable.

Item 33. The radio frequency identification tag of item 31, wherein the first and second electrode ends make crimp connections with the respective first and second terminals.

Item 34. The radio frequency identification tag of item 31, wherein the first substrate is disposed between the antenna and the meandering electrode.

Item 35. The radio frequency identification tag of item 31, wherein the first substrate is not disposed between the antenna and the meandering electrode.

Item 36. The radio frequency identification tag of item 24, wherein the second substrate is not disposed between the antenna and the meandering electrode.

Item 37. The radio frequency identification tag of item 36, wherein the second substrate is stretchable.

Item 38. The radio frequency identification tag of item 36, wherein the second substrate is not stretchable.

Item 39. The radio frequency identification tag of item 36, wherein the first substrate is disposed between the antenna and the meandering electrode.

Item 40. The radio frequency identification tag of item 36, wherein the first substrate is not disposed between the antenna and the meandering electrode.

Item 41. The radio frequency identification tag of item 36, wherein the second substrate comprises polyimide.

Item 42. The radio frequency identification tag of item 36, wherein the first and second electrode ends directly contact the respective first and second terminals.

Item 43. The radio frequency identification tag of item 36, wherein the first and second electrode ends make electrical connections with the respective first and second terminals using a conductive paste or adhesive.

Item 44. A radio frequency identification tag comprising:
a stretchable substrate having opposite major top and bottom surfaces;
an antenna having a plurality of substantially concentric loops disposed on the major top surface and comprising an innermost loop and an outermost loop, a radius of curvature of the antenna along at least 95% of each loop of the antenna being greater than about 0.1 mm and less than about 4 mm;
a first terminal disposed within the innermost loop and in electrical communication with a first end of the antenna;
a second terminal disposed outside the outermost loop and in electrical communication with a second end of the antenna;
a dielectric layer printed on the antenna leaving at least portions of the first and second terminals exposed; and
an electrically conductive wire, a first end of the wire attached to and making electrical connection with the first terminal, a second end of the wire attached to and making electrical connection with the second terminal, a gap being formed between the dielectric layer and the wire, the dielectric layer preventing the wire from contacting any of the loops of the antenna.

Item 45. A radio frequency identification tag comprising:
a stretchable substrate folded along a fold line to form top and bottom stretchable fold portions, each fold portion having major top and bottom surfaces, the major top surface of the bottom fold portion facing the major bottom surface of the top fold portion;
an antenna having a spiral form disposed on the major top surface of the top fold portion and having a length between first and second ends;
a first terminal disposed on the major top surface of the top fold portion and in electrical communication with the first end of the antenna;
a second terminal disposed on the major top surface of the top fold portion and in electrical communication with the second end of the antenna;
a meandering electrode disposed on the major bottom surface of the bottom fold portion and having first and second electrode ends, the first and second electrode ends making crimp connections with the respective first and second terminals.

Item 46. The radio frequency identification tag of item 45, wherein the antenna includes a plurality of substantially concentric loops disposed on the major top surface of the top fold portion and comprising an innermost loop, an outermost loop and a plurality of middle loops disposed between the innermost loop and the outermost loop, and wherein a radius of curvature of each middle loop along at least 95% of an entire length of the middle loop is greater than about 0.1 mm and less than about 4 mm.

Item 47. A radio frequency identification tag comprising:
a stretchable substrate folded along a fold line to form top and bottom stretchable fold portions facing each other;
an antenna having a length between first and second ends of the antenna disposed on a major first surface of the top fold portion, the antenna comprising a plurality of substantially concentric loops comprising a plurality of middle loops disposed between an innermost loop and an outermost loop, wherein a radius of curvature of each middle loop along at least 95% of an entire length of the middle loop is greater than about 0.1 mm and less than about 4 mm;
a first terminal disposed on the major first surface of the top fold portion and in electrical communication with the first end of the antenna;
a second terminal disposed on the major first surface of the top fold portion and in electrical communication with the second end of the antenna;
a meandering electrode disposed on a major surface of the bottom fold portion and having first and second electrode ends, the first and second electrode ends making electrical connections with the respective first and second terminals.

Item 48. A radio frequency identification tag comprising:
a stretchable substrate having opposite major top and bottom surfaces;
an antenna having a plurality of substantially concentric loops disposed on the major top surface and comprising an innermost loop and an outermost loop, a radius of curvature of the antenna along at least 95% of each loop of the antenna being greater than about 0.1 mm and less than about 4 mm;
a first terminal disposed within the innermost loop and in electrical communication with a first end of the antenna;
a second terminal disposed outside the outermost loop and in electrical communication with a second end of the antenna; and
a meandering electrode disposed on the major bottom surface and having first and second electrode ends, the first and second electrode ends making crimp connections with the respective first and second terminals.

Although specific embodiments have been illustrated and described herein, it will be appreciated by those of ordinary skill in the art that a variety of alternate and/or equivalent implementations can be substituted for the specific embodiments shown and described without departing from the scope of the present disclosure. This application is intended to cover any adaptations or variations of the specific embodiments discussed herein. Therefore, it is intended that this disclosure be limited only by the claims and the equivalents thereof.

What is claimed is:
1. A radio frequency identification tag comprising:
a stretchable substrate having opposite major top and bottom surfaces;
an antenna having a plurality of substantially concentric loops disposed on the major top surface and comprising an innermost loop and an outermost loop, a radius of curvature of the antenna along at least 90% of each loop of the antenna being greater than about 0.1 mm and less than about 5 mm;
a first terminal disposed within the innermost loop and in electrical communication with a first end of the antenna;
a second terminal disposed outside the outermost loop and in electrical communication with a second end of the antenna;
a dielectric layer printed on the antenna leaving at least portions of the first and second terminals exposed; and
an electrically conductive ink printed on and between the exposed portions of the first and second terminals and electrically connecting the first and second terminals, the dielectric layer preventing the conductive ink from contacting any of the loops of the antenna,
wherein the substantially concentric loops form a plurality of concentric first arcs having a same first arc angle and a plurality of concentric second arcs having a same second arc angle different than the first arc angle, the first arc angle being in a range from about 60 degrees to about 120 degrees, and the second arc angle being in a range from about 150 degrees to about 210 degrees.

2. The radio frequency identification tag of claim 1, wherein the radius of curvature of the antenna along at least 90% of each loop of the antenna is greater than about 0.1 mm and less than about 4 mm.

3. The radio frequency identification tag of claim 1, wherein the radius of curvature of the antenna along at least 95% of each loop of the antenna is greater than about 0.1 mm and less than about 5 mm.

4. The radio frequency identification tag of claim 1, wherein the radius of curvature of each middle loop along at least 98% of an entire length of the middle loop is greater than about 0.1 mm and less than about 4 mm.

5. The radio frequency identification tag of claim 1, wherein the antenna comprises a metal spiral trace forming the plurality of substantially concentric loops.

6. The radio frequency identification tag of claim 1, wherein the electrically conductive ink comprises metallic particles.

7. The radio frequency identification tag of claim 1, further comprising:
a first attachment area on the major bottom surface corresponding to and aligned with the first terminal;
a second attachment area on the major bottom surface corresponding to and aligned with the second terminal; and
a conductive wire having first and second ends attached to the respective first and second attachment areas and making crimp connections with the respective first and second terminals.

8. The radio frequency identification tag of claim 1, wherein the substantially concentric loops comprise a larger number of concentric first arcs and a smaller number of concentric second arcs.

9. The radio frequency identification tag of claim 8, wherein the first arc angle is in a range from about 80 to about 100 degrees and the second arc angle is in a range from about 170 degrees to about 190 degrees.

10. A radio frequency identification tag comprising:
a first stretchable substrate having opposite major top and bottom surfaces;
an antenna having a spiral form disposed on the major top surface and having a length between first and second ends;
a first terminal disposed on the major top surface and in electrical communication with the first end;
a second terminal disposed on the major top surface and in electrical communication with the second end;
a second substrate, discrete from the first stretchable substrate, having opposite major top and bottom surfaces, one of the major top and bottom surfaces of the second substrate facing one of the major top and bottom surfaces of the first stretchable substrate;
a meandering electrode disposed on one of the major top and bottom surfaces of the second substrate and having first and second electrode ends in registration and making electrical connections with the respective first and second terminals,
wherein the antenna comprises a plurality of substantially concentric loops forming a plurality of concentric first arcs having a same first arc angle and a plurality of concentric second arcs having a same second arc angle different than the first arc angle, the first arc angle being in a range from about 60 degrees to about 120 degrees, and the second arc angle being in a range from about 150 degrees to about 210 degrees.

11. The radio frequency identification tag of claim 10, wherein there is an air gap formed between the first stretchable substrate and the second substrate.

12. The radio frequency identification tag of claim 10, further comprising an integrated circuit disposed on the top or bottom surface of the second substrate in electrical communication with the meandering electrode.

13. The radio frequency identification tag of claim 10, wherein the plurality of substantially concentric loops comprise a plurality of middle loops disposed between an innermost loop and an outermost loop, wherein a radius of curvature of each middle loop along at least 95% of an entire length of the middle loop is greater than about 0.1 mm and less than about 4 mm.

14. The radio frequency identification tag of claim 10, wherein the meandering electrode comprises a pad portion along the length of the electrode between the first and second electrode ends for mounting an integrated circuit, the pad portion being in electrical communication with the electrode, such that except for the pad portion, a radius of curvature of the electrode along at least 95% of the length of the electrode between the first and second electrode ends is greater than about 0.1 mm and less than about 10 mm.

15. The radio frequency identification tag of claim 10, wherein the second substrate is disposed between the antenna and the meandering electrode.

16. The radio frequency identification tag of claim 10, wherein the first and second electrode ends make crimp connections with the respective first and second terminals.

17. The radio frequency identification tag of claim 10, wherein the first and second electrode ends make electrical connections with the respective first and second terminals using a conductive paste or adhesive.

18. A radio frequency identification tag comprising:
a stretchable substrate having opposite major top and bottom surfaces;
an antenna having a plurality of substantially concentric loops disposed on the major top surface and comprising an innermost loop and an outermost loop, a radius of curvature of the antenna along at least 95% of each loop of the antenna being greater than about 0.1 mm and less than about 4 mm;
a first terminal disposed within the innermost loop and in electrical communication with a first end of the antenna;

a second terminal disposed outside the outermost loop and in electrical communication with a second end of the antenna;

a dielectric layer printed on the antenna leaving at least portions of the first and second terminals exposed; and an electrically conductive wire, a first end of the wire attached to and making electrical connection with the first terminal, a second end of the wire attached to and making electrical connection with the second terminal, a gap being formed between the dielectric layer and the wire, the dielectric layer preventing the wire from contacting any of the loops of the antenna, wherein the substantially concentric loops form a plurality of concentric first arcs having a same first arc angle and a plurality of concentric second arcs having a same second arc angle different than the first arc angle, the first arc angle being in a range from about 60 degrees to about 120 degrees, and the second arc angle being in a range from about 150 degrees to about 210 degrees.

19. The radio frequency identification tag of claim 18, wherein the substantially concentric loops comprise a larger number of concentric first arcs and a smaller number of concentric second arcs.

20. The radio frequency identification tag of claim 10, wherein the meandering electrode has a substantially sinusoidal shape.

* * * * *